United States Patent [19]

Knips et al.

[11] Patent Number: 4,477,380
[45] Date of Patent: Oct. 16, 1984

[54] OXIDATION PROCESS OF REACTIVE AROMATICS WITH REACTIVATION OF THE CATALYST USING POTASSIUM PERMANGANATE

[75] Inventors: Ulrich Knips, Kamen-Heeren-Werve; Bertram Bohmer, Lunen; Roland Herzberg, Castrop-Rauxel, all of Fed. Rep. of Germany

[73] Assignee: Rutgerswerke Aktiengesellschaft, Fed. Rep. of Germany

[21] Appl. No.: 403,615

[22] PCT Filed: Mar. 23, 1982

[86] PCT No.: PCT/EP82/00058

§ 371 Date: Jul. 23, 1982

§ 102(e) Date: Jul. 23, 1982

[87] PCT Pub. No.: WO82/03625

PCT Pub. Date: Oct. 28, 1982

[30] Foreign Application Priority Data

Apr. 22, 1981 [DE] Fed. Rep. of Germany ....... 3115971
Mar. 3, 1982 [DE] Fed. Rep. of Germany ....... 3207572

[51] Int. Cl.³ ..................... C07C 46/04; C07C 51/265
[52] U.S. Cl. .................................. 260/385; 562/408; 562/414
[58] Field of Search ............. 562/416, 408, 414; 568/319; 260/385

[56] References Cited

U.S. PATENT DOCUMENTS 3,519,684 7/1970 Witt et al. .......................... 562/417
3,856,855 12/1974 Yamashita et al. ................ 562/416

FOREIGN PATENT DOCUMENTS 642459 9/1950 United Kingdom ............... 562/408
155492 6/1966 U.S.S.R. ............................. 562/414

OTHER PUBLICATIONS

Wiberg, ed., *Oxidation in Organic Chemistry, Part A*, p. 30, Academic Press, New York, 1965.
*Chemical Abstracts*, vol. 75, No. 1, Abstract No. 5576a, (1971), Robinson et al., "Liquid-Phase Oxidation of Condensed Aromatics."
*Patents Abstracts of Japan*, vol. 1, No. 157, p. 3503 (1977), Kokai, No. 52-101687, "Recovery of Catalyst."

*Primary Examiner*—Natalie Trousof
*Assistant Examiner*—Patricia M. Scott
*Attorney, Agent, or Firm*—Charles A. Muserlian

[57] ABSTRACT

In the oxidation of reactive aromatics with molecular oxygen in carboxylic acid solution in the presence of a catalyst consisting of a cobalt compound and possibly with addition of a manganese and a bromine compound suitable as Co-catalyst, an inactivation of the catalyst system readily occurs. This is prevented in that after each reaction cycle the catalyst is reactivated by treatment with a strong oxidant and the water formed in the reaction is removed by distillation.

6 Claims, No Drawings

OXIDATION PROCESS OF REACTIVE AROMATICS WITH REACTIVATION OF THE CATALYST USING POTASSIUM PERMANGANATE

The invention relates to a process of oxidizing reactive aromatics with molecular oxygen in the presence of a catalyst consisting of a cobalt compound in carboxylic acid and possibly with addition of a manganese and a bromine compound suitable as Co catalyst.

Reactive aromatics are those aromatic compounds which have one or more reactive carbon-hydrogen bonds. These may be either in methyl groups of a methyl-substituted aromatic, or in an aromatic nucleus. Examples of methyl-substituted reactive aromatics are toluene, xylenes, mono-alkyl naphthalenes such as 1-methyl naphthalene, or 2-methyl naphthalene, dimethyl naphthalenes such as 1,2-dimethyl naphthalene, 1,3-dimethyl naphthalene, 1,4-dimethyl naphthalene, 1,5-dimethyl naphthalene, 1,6-dimethyl naphthalene 1,7-dimethyl naphthalene, 1,8-dimethyl naphthalane, 2,3 dimethyl naphthalane, 2,6-dimethyl naphthalene or 2,7-dimethyl naphthalane, trimethyl naphthalenes or also methyl derivatives of higher annellated aromatics.

These products are oxidized to the respective carboxylic acids. Examples of reactive aromatics with reactive carbon-hydrogen bonds in an aromatic nucleus are anthracene as well as substituted anthracenes which do not have substituents oxidizable under the reaction conditions, such a halogen or nitro-anthracenes, or reactive multi-nucleus aromatics, such as fluorines or derivatives thereof. These compounds are oxidized to the respective quinones or ketones.

From DE-OS No. 2,107,357 a process is known for the oxidation of monomethyl or dimethyl naphthalenes with molecular oxygen. The oxidation takes place in aqueous, acetic acid solution using a catalyst which is composed of a cobalt, a manganese, and a bromine compound.

After completion of the reaction, a part of the acetic acid is distilled, the residue is mixed with much water, boiled out, and the mixture cooled, and the produced naphthalene carboxylic acid is precipitated and separated. The aqueous solution containing the catalyst is discarded. The process is labor-intensive and costly as to energy. Besides it is uneconomical to discard the catalyst after each reaction cycle.

The DE-OS No. 2,107,357 does indeed also indicate the possibility of recovering unreacted starting material, intermediate oxidation product and catalyst "by removal of water" and "recycling by subjecting the residual mother liquor to an oxidation treatment." However, considering the energy needed for evaporating the water, also this process step is not acceptable economically. Besides, it has been found that the catalyst solution thus re-used has lost almost its entire activity, so that a second reaction cycle with the same catalyst yields no appreciable conversion any more.

DE-AS No. 19 40 051 describes a process for the selective oxidation of anthracene fractions with molecular oxygen. The oxidation takes place in carboxylic solution using a catalyst composed of a cobalt, a manganese, and a bromine compound. No information is given about the processing of the catalyst system, but in view of its low price, the total loss is accepted.

The problem was, therefore, to find a simpler and more economical process for the oxidation of reactive aromatics which permits doing without the separation by distillation of relatively large quantities of solvent and using the catalyst solutions several times without an adverse loss of activity occurring.

The solution of the problem resides in a process for the oxidation of reactive aromatics with molecular oxygen in carboxylic acid solution in the presence of a catalyst consisting of a cobalt compound and possibly with addition of a manganese and a bromine compound suitable as Co catalyst, characterized in that after each reaction cycle the catalyst is reactivated by treatment with a strong oxidant and the water formed in the reaction is removed by distillation.

It has been found that the reason for the blocking of the catalyst system is that upon the oxidation of the aromatics due to secondary reactions or reactions of concomitants compounds are formed which bring about the formation of stable $Co^{3+}$ complexes. Cobalt(III) complexes are known to be more stable than simple cobalt(III) salts. This means: In these complexes the oxidation stage 3 of the cobalt is fixed in such a way that a transition to the bivalent state is prevented in the case of the carboxylic acid reaction medium at hand. Owing to this, the cobalt salt becomes inoperative as oxidation catalyst.

Now if the catalyst thus wholly or partially blocked is treated with a strong oxidant, then obviously the complexing by-products are oxidatively degraded to such an extent that simple cobalt(III) salts are formed again. When adding a new quantity of reactive aromatics, a new reaction cycle can take place. This reaction sequence can be repeated at least ten times before a final blocking of the catalyst by inactivation due to the formation of resinous by-products occurs or the increasing rise in viscosity of the reaction mixture due to concentration of concomitants of the reactive aromatics inhibits the production of crystallized carboxylic acids or quinones and in the extreme case makes it impossible.

The reactive aromatics can be used as separate substance as well as in any mixtures with one another. No special requirements are set for their purity either, i.e. the related non-reactive compounds boiling in approximately the same temperature range, as for instance naphthalene, diphenyl, phenanthrene or carbazole, do not interfere with the oxidation reaction. Likewise, removal of sulfur substances, as for instance methyl thionaphthalene or thionaphthene, is not necessary. The oxidation of the reactive aromatics is carried out in an acetic acid solution, using per part by weight of reactive aromatics at least 2.5 parts by weight of acetic acid. The acetic acid may contain small quantities of water, as this improves the solubility of the salts used as catalyst. On the other hand, the yield of end product decreases with increasing water content of the reaction solution. For this reason, that quantity of water is sufficient which is contributed when the salts serving as catalyst are used with their natural water of crystallization content. Besides, during the oxidation reaction water is formed, which dilutes the acetic acid. It is advisable to remove this water before the next reaction cycle.

As catalyst for the oxidation reaction one uses a combination of compounds which contains the three components—a cobalt compound (component A), a manganese compound (component B) and bromine or a bromine compound (component C)—in certain proportions.

The proportional quantities of the individual components A, B and C are comprised in the following ranges:

$$1.0 \leq X+Y+Z \leq 10.0 \quad (1)$$

$$0.1 \leq Z/(X+Y) \leq 2.5 \quad (2)$$

and $$0.2 \leq X/Y \leq 20 \quad (3)$$

Herein X denotes the quantity of the cobalt contained in the cobalt compound named, stated in parts by weight per 50 parts by weight of reactive aromatics; Y denotes the quantity of manganese contained in the manganese compound, stated in parts by weight per 50 parts by weight of reactive aromatics, and Z the quantity of bromine or of the bromine contained in the bromine compound, stated in parts by weight per 50 parts by weight of reactive aromatics.

Examples of suitable cobalt (component A) or manganese compounds (component B) that can be used in the catalyst according to the invention are cobalt and manganese salts of aliphatic carboxylic acids with 1 to 4 carbon atoms, e.g. formic, acetic, propionic, butyric, succinic acid, cobalt and manganese salts of aromatic carboxylic acids, e.g. benzoic acid, phthalic acid, naphthalene-monocarboxylic acid or naphthalene-dicarboxylic acid, and inorganic salts of cobalt and manganese, e.g. oxides, carbonates, basic carbonates, chlorides and bromides.

Preferred salts are cobalt(II) and manganese(II) acetate and bromide. The use of a cobalt or manganese bromide has the advantage that thereby simultaneously the component C of the catalyst is brought in. But if only cobalt bromide and manganese bromide are used as components (A), (B) and (C), the proportional ratio between cobalt, manganese and bromine which is to be supplied to the reaction system does not fulfill the condition that is prescribed by the above stated formula (2). Accordingly it is necessary to use suitable quantities of other compounds of cobalt and/or manganese, besides cobalt and manganese bromide (e.g. cobalt and manganese acetate) together with cobalt and/or manganese bromide and to adjust the proportional ratio among these compounds in such a way that X, Y and Z fulfill the conditions prescribed by the formulas (1), (2) and (3).

Instead of cobalt or manganese bromide it is possible also to use bromine or another bromine compound as component C of the catalyst, such as other metal bromides, ammonium bromide, hydrogen bromide, or organic bromine compounds as for example bromoacetic acid or benzyl bromide.

The oxidation of the aromatics is effected by oxygen. One uses molecular oxygen, either as pure oxygen or in mixture with one or more gases inert to the reaction. Such a mixture is air.

It is necessary to carry out the oxidation of the reactive aromatics under pressure, namely in such a way that the partial pressure of the oxygen is at least 0.5 bar. If the oxygen partial pressure is lower than 0.5 bar, the yield of the desired oxidation products is reduced. The preferred oxygen partial pressure is within the range of from 1 to 10 bar, in particular 2 to 8 bar. While at an oxygen partial pressure of more than 10 bar one obtains oxidation products also, the yield is not appreciably increased by increasing the oxygen partial pressure beyond the above stated upper limit, so that a further increase of the pressure serves no economic purpose. Hence this process permits e.g. the production of anthraquinone under a much milder pressure than in DE-AS 19 40 051 under the optimum experimental conditions documented in the examples.

To achieve an economically sufficient reaction velocity, it is necessary to carry out the oxidation of the anthracene at a temperature above 70° C. On the other hand, the reaction temperature should not exceed 170° C., as otherwise the proportion of the resulting undesirable by-products becomes too great.

Accordingly the oxidation of the reactive aromatics is effected in that the latter, acetic acid, and the catalyst combination are charged in a pressure vessel and heated. Before or after the heating, oxygen or a gas containing oxygen is injected into the reactor, and the selected pressure is maintained during the entire reaction time.

Expediently one composes the reaction mixtures in such a way as to still achieve a complete conversion of the charged reactive aromatic per reaction cycle before the catalyst is blocked. This can be achieved by using the catalyst mixture in a quantity of 10-2 wt.% of the charged aromatic. The reaction is completed when oxygen is no longer absorbed.

After this first reaction cycle there occurs an aftertreatment of the reaction mixture with an oxidant. The inhibiting by-products are thereby oxidatively degraded to such an extent that after addition of fresh reactive aromatic a new reaction cycle can take place. As oxidants are suitable those with a strong oxidation potential, as for example ozone, per acids, peroxy disulfates, or chromic acid.

Preferably potassium permanganate is used, which has the advantage that except for potassium ions, which do not interfere, no other extraneous ions get into the reaction mixture, as the manganese is already a component part of the catalyst. At the same time it serves to compensate catalyst losses.

The regeneration of the catalyst is conveniently effected at elevated temperature and can advantageously be combined with the removal of the water of reaction, in that simultaneously an acetic acid/water, or—after addition of benzene—a benzene/water azeotrope is separated by distillation.

Thereafter the catalyst is ready for use in the second reaction cycle. At least 5 to 10 such cycles can be carried out with one catalyst batch before a final blocking of the catalyst occurs by inactivation due to resinification. The number of reaction cycles that can be carried out depends essentially on the degree of viscosity increase of the reaction mixture. It is found in this connection that mixtures of the reactive aromatics naturally cause a more frequent processing than the pure aromatics, where secondary reactions of the concomitants occur to a lesser extent.

The solubility of the oxidation products is so low in the cooled reaction mixture that after each reaction cycle partially the entire quantity of formed carboxylic acids or quinones crystallizes out. Residual quantities do not interfere with the reaction and are quite stable to boiling with $KMnO_4$ under the existing conditions. This offers the additional advantage of the process that the activated catalyst can be recycled without further purification and that thereby a simple intermittent or continuous process conduction becomes possible.

If after the last reaction cycle the crystallization of the oxidation product during cooling is rendered very difficult, it is expedient to mix with water, whereupon the still dissolved oxidation product with the accumulated concomitants precipitates in amorphous or microcrystalline form. Previously the acetic acid may, if desired, be distilled to a large extent. From the aqueous solution the catalyst salts can be recovered. The expedient process sequence will become evident from the examples.

EXAMPLES

EXAMPLE 1

Into a heatable pressure apparatus equipped with an agitator, of a capacity of 0.2 liter, introduce 10 g 2-methyl naphthalene and a solution of 50 g acetic acid, 1.5 g $Co(CH_3COO)_2.4H_2O$ and 0.5 g $MnBr_2.4H_2O$. Then close the reaction vessel, gasify with 2 bar oxygen, and heat to 130° C. During this procedure regulate the pressure to 2 bar through a compensating valve. After a reaction time of 1½ hours, cool to about 80° C. and expand.

Then add 0.5 g solid $KMnO_4$ and 15 ml glacial acetic acid, thereby causing azeotropic distillation of the water of reaction. Stop after 15 ml have passed over in slow distillation.

For the second reaction cycle, again add 10 g 2-methyl naphthalene, gasify with 2 bar oxygen, and heat to 130° C. for 2½ hours. Thereafter, as in reaction cycle 1, regenerate the catalyst with the aid of 0.5 g $KMnO_4$ and re-use the reaction solution.

After the third reaction cycle, cool the mixture to room temperature after the pressure gasification, suction-filter the crystal mass, and subject the solution to the usual removal of water and catalyst regeneration after addition of 0.5 g $Co(CH_3COO)_2.4H_2O$.

A total of five reaction cycles are carried out with the same catalyst batch. Thereafter the reaction mixture is cooled and the precipitated naphthoic acid filtered off. The filtrate is admixed with 500 ml cold water and this precipitated naphthoic acid, too, is filtered off, washed with plenty of water and dried.

Yield: 46.2 g naphthoic acid-(2)
Purity: 85%
corresponding to 65% of the theory.

EXAMPLE 2

As in Example 1, in a 1-liter apparatus 100 g 1-methyl naphthalene in 250 g acetic acid, which contains in solution 25 g $Co(CH_3COO)_2.4H_2O$ and 2.5 g $MnBr_2.4H_2O$, are gasified with 2 bar oxygen at 125° C. within 6 hours. The product is expanded and cooled to room temperature. The resulting crystal paste of crude naphthoic acid is suction-filtered.

After admixing the reaction solution with 2.5 g solid $KMnO_4$, heat to 100° C. and remove the water of reaction by distillation with little acetic acid (20 g in all). The solution thus obtained is again admixed with 100 g methyl naphthalene and acetic acid (to replenish the quantity eliminated during dewatering) and subjected to oxygen gasification.

After a total of 5 reaction cycles, the greater part of the acetic acid is removed by distillation and the residue extracted with water to recover the catalyst salts. The naphthoic acid remaining in the insoluble part can be extracted with dilute NaOH solution.

In the course of all five reaction cycles 500 g crude acid of a 90% purity can be obtained, corresponding to a yield of 74%.

EXAMPLE 3

With a procedure analogous to Example 2, in five reaction cycles 50 g of a 95% 2,6-dimethyl naphthalene material are subjected to oxidation. Portions of 10 g of the aromatic in a mixture consisting of 50 g glacial acetic acid, 2.5 g $Co(CH_3COO)_2.4H_2O$ and 0.5$MnBr_2.4H_2O$ are caused to react at 125° C. and 4 bar oxygen pressure. The reactivation of the catalyst is effected with 0.5 g $KMnO_4$ each time.

EXAMPLE 4

In analogy to Example 1, in a 1-liter apparatus are charged 50 g anthracene (95%) and a solution of 150 g acetic acid, 7.5 g $Co(CH_3COO)_2.4H_2O$ and 1.3 g $MnBr_2.4H_2O$. Then the reactor is closed, gasified with 2 bar oxygen, and heated to 130° C. Through a compensating valve the pressure is regulated to 4 bar during this process. After a reaction time of 5–6 hours, cool to about 90° C. and expand.

Then add 1 g solid $KMnO_4$ and 25 ml glacial acetic acid, thereby distilling the water of reaction. Stop when in slow distillation about 25 ml have passed over. Thereafter the mixture is cooled to room temperature, the crystal mass is suction-filtered, and the solution again subjected to pressure gasification after addition of 50 g anthracene.

In all, eleven reaction cycles were carried out with the same catalyst batch, the results of which are summarized in the following table.

| No. of reaction cycle | Anthracene charge (g) | Yield of anthraquinone (based on 100% product) | | Content of phenanthrene (%) |
|---|---|---|---|---|
| | | (g) | (% of theory) | |
| 1 | 50 | 38.3 | 68.9 | — |
| 2 | 50 | 45.3 | 81.6 | 0.3 |
| 3 | 50 | 44.3 | 79.8 | 0.6 |
| 4 | 50 | 39.1 | 70.4 | 0.7 |
| 5 | 50 | 48.1 | 86.6 | 0.5 |
| 6 | 50 | 46.2 | 83.3 | 1.2 |
| 7 | 50 | 47.9 | 86.3 | 0.9 |
| 8 | 50 | 47.4 | 85.4 | 0.7 |
| 9 | 50 | 47.0 | 84.6 | 0.3 |
| 10 | 50 | 44.2 | 79.5 | 0.5 |
| 11 | 50 | 46.3 | 83.4 | 0.5 |

As the results of the eleventh reaction cycle show, the reactivity of the catalyst mixture is by no means exhausted.

We claim:

1. In a process for the oxidation of reactive aromatic components at 70° to 170° C. in solution in a carboxylic acid in the presence of a cobalt catalyst optionally containing a manganese compound and a bromine compound as cocatalyst with molecular oxygen, the proportional values of the catalyst component having the following ranges $$1.0 \leq X+Y+Z \leq 10.0 \quad (1)$$

$$0.1 \leq Z/(X+Y) \leq 2.5 \quad (2)$$

$$0.2 \leq (X/Y) \leq 20 \quad (3)$$

wherein X is the amount by weight of cobalt per 50 parts by weight of reactive aromatic, Y is the amount by weight of manganese per 50 parts by weight of reactive aromatic and Z is the amount by weight of bromine per 50 parts by weight of reactive aromatics, the improvement comprising treating the catalyst solution with potassium permanganate at about 80° to 100° C. and removing the water of reaction by distillation before recycle to the oxidation step.

2. The process of claim 1 wherein the aromatic component is anthracene.

3. The process of claim 1 wherein the aromatic component is monomethylnaphthalene.

4. The process of claim 1 wherein the aromatic component is a dimethylnaphthalene.

5. The process of claim 1 wherein the catalyst contains soluble salts of cobalt and magnesium and contains bromide ions.

6. The process of claim 5 wherein the catalyst is comprised of cobalt diacetate and magnesium bromide.

* * * * *